United States Patent
Norris et al.

[11] Patent Number: 6,080,756
[45] Date of Patent: Jun. 27, 2000

[54] POLYMORPHS OF THE PRODRUG 6-N-(L-ALA-L-ALA)-TROVAFLOXACIN

[75] Inventors: Timothy Norris, Gales Ferry; James J. McGarry, Ledyard; Douglas J. M. Allen, New London, all of Conn.

[73] Assignee: Pfizer Inc., New York, N.Y.

[21] Appl. No.: 09/011,370

[22] PCT Filed: Jul. 5, 1996

[86] PCT No.: PCT/IB96/00653

§ 371 Date: Jan. 30, 1998

§ 102(e) Date: Jan. 30, 1998

[87] PCT Pub. No.: WO97/08191

PCT Pub. Date: Mar. 6, 1997

Related U.S. Application Data

[60] Provisional application No. 60/005,109, Aug. 29, 1995.

[51] Int. Cl.[7] ............... A61K 31/4375; A61P 31/04; C07D 471/04
[52] U.S. Cl. ............................... 514/300; 546/123
[58] Field of Search ............... 514/300; 546/123

[56] References Cited

U.S. PATENT DOCUMENTS

| 5,164,402 | 11/1992 | Brighty | ................. 514/300 |
| 5,229,396 | 7/1993 | Brighty | ................. 573/300 |

*Primary Examiner*—Evelyn Mei Huang
*Attorney, Agent, or Firm*—Peter C. Richardson; Paul H. Gingburg; Bryan C. Zielinski

[57] ABSTRACT

The invention relates to a monohydrate polymorph PII.M of a compound of the formula

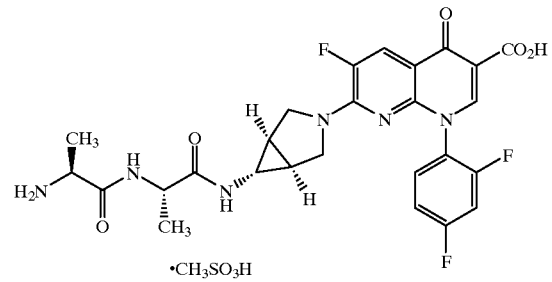

exhibiting the following X-ray powder diffraction pattern

| Peak No. | 1 | 2 | 3 | 4 | 5 | 6 | 7 | 8 |
|---|---|---|---|---|---|---|---|---|
| 2_θ_(°) Cu | 3.6 | 7.3 | 13.7 | 14.5 | 17.1 | 21.) | 23.6 | 26.7 |
| d space | 24.2 | 12.2 | 6.5 | 6.1 | 5.2 | 4.2 | 3.8 | 3.3 |

The invention also relates to methods of preparing the above compound, pharmaceutical compositions containing the above compound, and methods of treating bacterial infections by administering the above compound.

10 Claims, No Drawings

POLYMORPHS OF THE PRODRUG 6-N-(L-ALA-L-ALA)-TROVAFLOXACIN

This application claims benefit of provisional application Ser. No. 60/005,109 filed Aug. 29, 1995.

This application is the National phase of PCT/IB96/00653, filed on Jul. 5, 1996.

BACKGROUND OF THE INVENTION

This invention relates to a prodrug of trovafloxacin having the formula

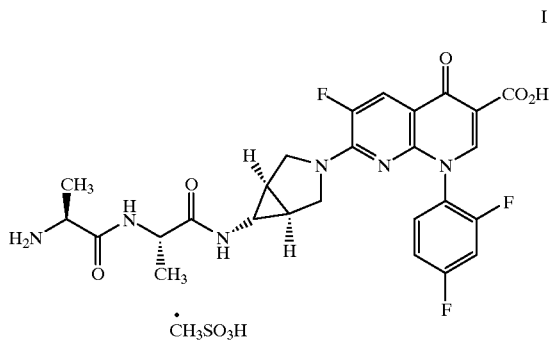

selected from the group consisting of polymorph PII and the monohydrate PII.M and pseudomorph PII.PS thereof and processes for their preparation. The invention further relates to methods of using, and pharmaceutical compositions comprising, the compounds of the invention for treatment of bacterial infections in mammals.

The antibacterial activity of trovafloxacin is described in U.S. Pat. Nos. 5,164,402 (the '402 patent) and 5,229,396 (the '396 patent) issued Nov. 17, 1992 and Jul. 20, 1993, respectively, the disclosures of which are hereby incorporated herein by reference in their entirety. The foregoing patents are assigned in common with the present application. A polymorph PI of the compound of formula I and methods for its preparation are also described in the above-indicated patents.

SUMMARY OF THE INVENTION

In a first embodiment the present invention relates to a prodrug of trovafloxacin having the formula

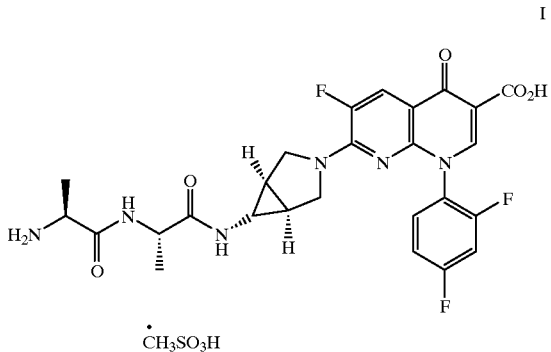

wherein said prodrug is selected from the group comprising a) a polymorph PII exhibiting the following X-ray powder diffraction pattern

| Peak no. | 1 | 2 | 3 | 4 | 5 | 6 | 7 | 8 | 9 |
|---|---|---|---|---|---|---|---|---|---|
| 2_θ_ (°) Cu | 3.4 | 6.8 | 13.5 | 16.8 | 19.6 | 20.3 | 23.1 | 25.7 | 27.8 |
| d space | 26.0 | 13.1 | 6.6 | 5.3 | 4.5 | 4.4 | 3.8 | 3.5 | 3.2 | b) a monohydrate PII.M exhibiting the following X-ray powder diffraction pattern

| Peak no. | 1 | 2 | 3 | 4 | 5 | 6 | 7 | 8 |
|---|---|---|---|---|---|---|---|---|
| 2_θ_(°) Cu | 3.6 | 7.3 | 13.7 | 14.5 | 17.1 | 21.0 | 23.6 | 26.7 |
| d space | 24.2 | 12.2 | 6.5 | 6.1 | 5.2 | 4.2 | 3.8 | 3.3 |

; and c) a pseudomorph PII.PS exhibiting the following X-ray powder diffraction pattern According to a second embodiment of the invention there is provided a process for preparing prodrug PII, as described above, which comprises treating the prodrug, PI, of the formula I, exhibiting the X-ray powder diffraction pattern, below, with dry ethanol.

According to another aspect, of the above embodiment, the invention provides a process for preparing a monohydrate, PII.M, as described above, of the polymorph, PII, which comprises a) treating the polymorph PI with an aqueous solvent;

b) treating the polymorph PII with water; or c) treating a pseudomorph of PII.M, PII.PS, with water.

Yet another aspect, of the above embodiment of the invention provides a process for preparing a pseudomorph, PII.PS, as described above, of the monohydrate PII.M. which comprises vacuum drying the monohydrate PII.M.

The invention also provides pharmaceutical compositions comprising an antibacterially effective amount of a compound of formula I, as described above, together with a pharmaceutically acceptable diluent or carrier.

In another embodiment the invention provides a method for treating bacterial infection in a mammal which comprises administering to said mammal a bacterial infection treating effective amount a compound of formula I, as described above.

A third embodiment of the invention provides a prodrug of trovafloxacin consisting of the polymorph PII, characterized by the X-ray diffraction pattern, described above, which is prepared by treating the polymorph PI, characterized by the X-ray diffraction pattern described above, with dry ethanol.

According to another aspect of the above embodiment there is provided a prodrug of trovafloxacin consisting of the monohydrate PII.M of polymorph PII, characterized by the X-ray diffraction pattern described above, which is prepared by a) treating the polymorph PI, characterized by the X-ray diffraction pattern described above, with an organic solvent containing water;

b) treating the polymorph PII with water; or c) treating the pseudomorph PII.PS, of PII.M, with water.

Yet another aspect of the above embodiment provides a prodrug of trovafloxacin consisting of its pseudomorph PII.PS characterized by the X-ray diffraction pattern described above, which is prepared by vacuum drying the monohydrate PII.M.

DETAILED DESCRIPTION OF THE INVENTION

This invention relates to a prodrug, of trovafloxacin, having the formula

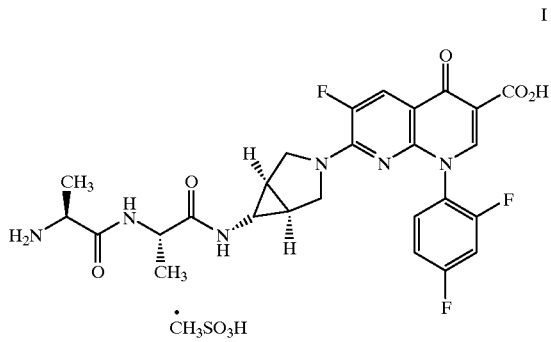

I selected from the group consisting a polymorph PII and the monohydrate PII.M and pseudomorph PII.PS thereof and pharmaceutical compositions comprising PII, PII.M or PII.PS and methods for using them. The invention also relates to processes for preparing PII, PII.M and PII.PS as illustrated in the following reaction scheme.

SCHEME 1

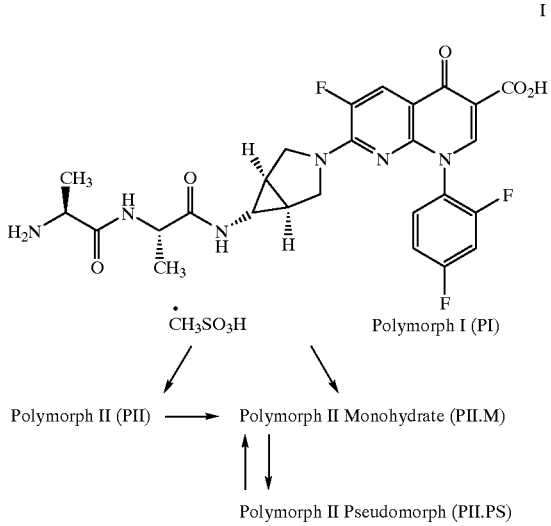

Referring to Scheme I polymorph PI is converted to polymorph PII by treatment with dry ethanol. The conversion is conveniently effected at about room temperature. Polymorph PI may be prepared according to the method of Example 49 of the '402 patent or co-pending U.S. Patent application docket number PC9186 the disclosures of which is hereby incorporated herein by reference in its entirety. The PC9186 application is assigned in common with the present application. Polymorph PII can then be converted to the monohydrate PII.M by treatment with water. The water may be in the form of a liquid or vapor.

Alternatively, the monohydrate, PII.M, can be prepared by treatment of polymorph PI with organic solvents, such as $(C_1-C_6)$alkyl esters of $(C_1-C_6)$alkanoic acids and $(C_1-C_6)$ alkanols, containing water at a temperature from about ambient to the reflux temperature of the solvent. A preferred solvent is ethyl acetate containing about 0.1% water and the conversion is effected at about 40–50° C., preferably about 45° C. Excess water is removed from the product by azeotropic distillation at the reflux temperature of the solvent. Another preferred solvent is ethanol containing about 5% water or less. The conversion is effected by treating PII with the solvent at its reflux temperature (about 78° C.) and the product is recovered, as crystal, upon cooling the solution.

The resultant crystals are dried to a water content of about 2.7% to yield the desired product.

The monohydrate PII.M can be converted to a pseudomorph PII.PS by vacuum drying. The pseudomorph can be reconverted to the monohydrate by treatment with liquid water as indicated above with respect to the conversion of PII to PII.M.

The antibacterial compounds of formula I, i.e., polymorph PII, monohydrate PII.M and pseudomorph PII.PS, (hereafter "the active compounds") that can be synthesized using the methods and intermediates of this invention are useful in the treatment of animals, and humans having a broad spectrum of bacterial infections. They are particularly useful in treating gram-positive bacterial strains.

The active compounds may be administered alone, but will generally be administered in a mixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, the compounds of formula I can be administered intramuscularly or subcutaneously at dosage levels of about 0.1 to about 50 mg/kg/day, advantageously about 0.2 to about 10 mg/kg/day given in a single daily dose or up to 3 divided doses.

The active compounds can be administered to humans, for the treatment of bacterial diseases by either oral or parenteral routes. They may be administered orally at dosage levels of about 0.1 to 500 mg/kg/day, advantageously 0.5–50 mg/kg/day given in a single dosage or up to 3 divided dosages. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the methods and compounds of the present invention. It will be understood, however, that the invention is not limited to the specific.

EXAMPLE 1

L-Alanyl-N-{(1α,5α,6α)-3-[6-carboxy-8-(2,4-difluorophenyl)-3-fluoro-5,8-dihydro-5-oxo-1,8-naphthyridin-2-yl]-3-azabicyclo[3.1.0]hex-6-yl}-N'-tert-butyloxycarbonyl-L-alaninamide The zwitterion of trovafloxacin (prepared as described in co-pending application docket number PC9186(3 g) was stirred with dichloromethane (45 mL) at about 25° C. to form a white slurry. N-tert-butyloxycarbonyl-L-alanyl-L-alanine (2.19 g) and 2-ethoxy-1-ethoxycarbonyl-1,2-dihydroquinoline (1.95 g) were added to the slurry and the resultant reaction mixture stirred for 4 hours at about 25° C. The reaction mixture was cooled to about 5° C. for 1 hour and the title product isolated as white crystals by filtration. The crystals were washed with dichloromethane (about 15 mL) and dried under vacuum. Yield 4.7 g, 80%.

EXAMPLE 2

L-Alanyl-N-{(1α,5α,6α)-3-[6-carboxy-8-(2,4-difluorophenyl)-3-fluoro-5,8-dihydro-5-oxo-1,8-naphthyridin-2-yl]-3-azabicyclo[3.1.0]hex-6-yl}-L-alaninamide methanesulfonate The title compound of Example 1 (10 g) and tetrahydrofuran (60 mL) were stirred to form a slurry at about 25° C. Methanesulfonic acid (2.9 g) was added to the slurry and the resultant reaction mixture heated to reflux (about 66° C.) for about 6 hours. The reaction mixture was cooled to about 5° C. and the crystals of the title product isolated by filtration, washed with cold tetrahydrofuran (about 15 mL) and dried under vacuum at 40° C. Yield 9.4 g, 94%.

EXAMPLE 3

L-Alanyl-N-{(1α,5α,6α)-3-[6-carboxy-8-(2,4-difluorophenyl)-3-fluoro-5,8-dihydro-5-oxo-1,8-naphthyridin-2-yl]-3-azabicyclo[3.1.0]hex-6-yl}-L-alaninamide methanesulfonate The title product of Example 1 (10 g), acetone (80 mL) and water (1.8 mL) were stirred to form a slurry at temperature of about 20° C. Methanesulfonic acid (4.4 g) was added to the slurry and the resultant reaction mixture heated to reflux (about 56° C.) for about 4 hours. Additional acetone (40 mL) was added to the reaction mixture during the reflux period. The reaction mixture was cooled to about 5° C. and the resultant crystals of the title product were isolated by filtration, washed with cold acetone (about 25 mL) and dried under vacuum at about 35° C. Yield 9.9 g, 93%.

EXAMPLE 4

L-Alanyl-N-{(1α,5α,6α)-3-[6-carboxy-8-(2,4-difluorophenyl)-3-fluoro-5,8-dihydro-5-oxo-1,8-naphthyridin-2-yl]-3-azabicyclo[3.1.0]hex-6-yl}-N'-tert-butyloxycarbonyl-L-alaninamide 7-([1α,5α,6α]-6-Amino-3-naphthyridin-2-yl]-3-azabicyclo[3.1.0]hex-3yl)-6-fluoro-1-(2,4-difluorophenyl)-1,4-dihydro-4-oxo-1,8-naphthyridine-3-carboxylic acid, methanesulfonate (40 g) was stirred with dichloromethane (600 mL) at about 20° C. to form a white slurry. Triethylamine (7.9 g), N-tert-butyloxycarbonyl-L-alanyl-L-alanine (23.76 g) and 2-ethoxy-1-ethoxycarbonyl-1,2-dihydroquinoline (21.14 g) were added to the slurry and the resultant reaction mixture was stirred for about 16 hours at about 25° C. The reaction mixture was cooled to about 5° C. for 1 hour and the title product isolated as white crystals by filtration. The crystals were washed with dichloromethane (about 80 mL) and dried under vacuum. Yield 42.6 g, 83%.

EXAMPLE 5

Polymorph PII of L-Ala-N-{(1α,5α,6α)-3-[6-carboxy-8-(2,4-difluorophenyl)-3-fluoro-5,8-dihydro-5-oxo-1,8-naphthyridin-2-yl]-3-azabicyclo[3.1.0]hex-6-yl}-L-alaninamide methanesulfonate The title product of Example 2 or 3 was stirred in dry (water content less than about 0.1%) ethanol (2.0 mL) for 48 hours at about 25° C. The title product was isolated by filtration.

The product is a characterized by the X-ray diffraction pattern described above.

EXAMPLE 6

Monohydrate of Polymorph II (PII.M)

A. The title product of Example 2 or 3 (4 g) was heated to reflux (about 78° C.) in ethanol containing water (≦5) (40 mL) for about 1 hour. A further quantity of ethanol (8 mL) was added during the reflux period to obtain solution. The reaction mixture was cooled to about 25° C. to obtain a crystal slurry. The crystals were isolated by filtration and dried to a water content of 2.7% to obtain the title product. Yield 90%.

B. The title product of Example 2 or 3 (20 g) was heated to about 45° C. in ethyl acetate (300 mL). Water (21 mL) was then slowly added to form a slurry. The slurry was heated to reflux and the water (about 19 mL) azeotropically removed. The solution was cooled to about 25° C. to obtain a crystal slurry. The crystals were isolated by filtration and dried to a water content of about 2.7% to obtain the title product. Yield 99%.

The title product is characterized by the X-ray diffraction pattern described above.

EXAMPLE 7

Pseudomorph PII.PS of Polymorph II Monohydrate

The title product of Example 6 was dried under vacuum until all the water was removed yielding the title product. The title product is characterized by the X-ray diffraction pattern described above.

What is claimed is:

1. A monohydrate polymorph PII.M of a compound of the formula

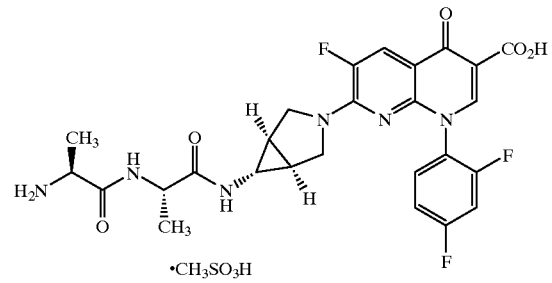

exhibiting the following X-ray powder diffraction pattern

| Peak No. | 1 | 2 | 3 | 4 | 5 | 6 | 7 | 8 |
|---|---|---|---|---|---|---|---|---|
| 2_θ_(°) Cu | 3.6 | 7.3 | 13.7 | 14.5 | 17.1 | 21.) | 23.6 | 26.7 |
| d space | 24.2 | 12.2 | 6.5 | 6.1 | 5.2 | 4.2 | 3.8 | 3.3 |

2. A process for preparing prodrug polymorph monohydrate PII.M, of trovafloxacin, for the formula of claim 1, which comprises (a) preparing polymorph PII exhibiting the X-ray powder diffraction pattern

| Peak no. | 1 | 2 | 3 | 4 | 5 | 6 | 7 | 8 | 9 |
|---|---|---|---|---|---|---|---|---|---|
| 2_θ_(°) Cu | 3.4 | 6.8 | 13.5 | 16.8 | 19.6 | 20.3 | 23.1 | 25.7 | 27.8 |
| d space | 26.0 | 13.1 | 6.6 | 5.3 | 4.5 | 4.4 | 3.8 | 3.5 | 3.2 | by treating the prodrug polymorph PI exhibiting the X-ray powder diffraction pattern.

3. The process of claim 2 step b) wherein said organic solvent is selected from the group consisting of $(C_1–C_6)$ alkyl esters of $(C_1–C_6)$ alkanoic acids and $(C_1–C_6)$ alkanols.

4. The process of claim 3 wherein said solvent is ethyl acetate.

5. A process for preparing prodrug polymorph monohydrate PII.M of claim 1 exhibiting the X-ray diffraction pattern described as follows:

| Peak no. | 1 | 2 | 3 | 4 | 5 | 6 | 7 | 8 |
|---|---|---|---|---|---|---|---|---|
| 2_θ_(°) Cu | 3.6 | 7.3 | 13.7 | 14.5 | 17.1 | 21.0 | 23.6 | 26.7 |
| d space | 24.2 | 12.2 | 6.5 | 6.1 | 5.2 | 4.2 | 3.8 | 3.3 | which comprises treating the prodrug polymorph PI exhibiting the X-ray diffraction pattern described as follows:

| Peak No. | 1 | 2 | 3 | 4 | 5 | 6 | 7 | 8 |
|---|---|---|---|---|---|---|---|---|
| 2_θ_(°) Cu | 6.1 | 7.3 | 7.9 | 9.5 | 11.7 | 14.2 | 14.9 | 15.8 |
| d space | 14.5 | 12.1 | 11.2 | 9.3 | 7.6 | 6.2 | 6.0 | 5.6 |

| Peak No. | 9 | 10 | 11 | 12 | 13 | 14 |
|---|---|---|---|---|---|---|
| 2_θ_(°) Cu | 16.8 | 20.1 | 21.4 | 22.7 | 24.9 | 26.0 |
| d space | 5.3 | 4.4 | 4.2 | 3.9 | 3.6 | 3.4 | with an organic solvent containing water.

6. The process of claim 5 wherein said organic solvent is a $C_1–C_6$ alkyl ester of a $C_1–C_6$ alkanoic acid or a $C_1–C_6$ alkanol.

7. The process of claim 6 wherein said solvent is ethyl acetate.

8. A method for treating bacterial infection in a mammal in need thereof which comprises administering to said mammal a bacterial infection treating effective amount of the prodrug of claim 1.

9. A pharmaceutical composition for treating bacterial infection in a mammal comprising a bacterial infection treating effective amount of the prodrug of claim 1 and a pharmaceutically acceptable carrier.

10. The compound of claim 1 having a water content of about 2.7%.

* * * * *